United States Patent [19]
Ring

[11] 3,981,305
[45] Sept. 21, 1976

[54] LOW DENSITY TAMPON OF INTERMESHED DEFORMABLE STRIP MATERIAL AND INSERTER THEREFOR

[75] Inventor: David F. Ring, Neenah, Wis.

[73] Assignee: Kimberly-Clark Corporation, Neenah, Wis.

[22] Filed: Sept. 11, 1975

[21] Appl. No.: 612,488

[52] U.S. Cl. .............................. 128/285; 128/130; 128/270
[51] Int. Cl.² .......................................... A61F 13/20
[58] Field of Search ....... 128/130, 263, 270, 290 W, 128/290 P, 2 B, 285

[56] References Cited
UNITED STATES PATENTS

| | | | |
|---|---|---|---|
| 2,412,861 | 12/1946 | Beadle et al. | 128/285 |
| 3,397,695 | 8/1968 | Voss | 128/285 |
| 3,731,687 | 5/1973 | Glassman | 128/285 |

FOREIGN PATENTS OR APPLICATIONS

| | | | |
|---|---|---|---|
| 349,885 | 6/1931 | United Kingdom | 128/270 |

*Primary Examiner*—Aldrich F. Medbery
*Attorney, Agent, or Firm*—Daniel J. Hanlon, Jr.; William D. Herrick; Raymond J. Miller

[57] ABSTRACT

A self-expanding low density catamenial tampon made up of intermeshing loops of resiliently deformable strip material. The intermeshed loops are arranged in the form of an openwork spheroid with the strips crossing at the top and bottom of the vertical axis of the spheroid. The strips at the bottom crossing area are secured together by a withdrawal string.

A special inserter for the tampon is also described, the inserter is comprised of a tubular tampon-containing member and an internal pusher element in slidable association with the tube member and having an axial tampon-supporting frontal extension thereon. When combined with the inserter the spheroidal tampon is collapsed with the top and bottom crossover areas juxtaposed. The elongate tampon-supporting pusher element is positioned at the bottom crossover point and the rest of the tampon is folded down around the element to form the tampon into an inverted cup shape. The cup-shaped tampon is then pushed into the outer tubular member by the pusher element. The tubular member is of lesser diameter than the uncompressed folded tampon and therefore holds the tampon in resiliently compressed condition therein.

20 Claims, 9 Drawing Figures

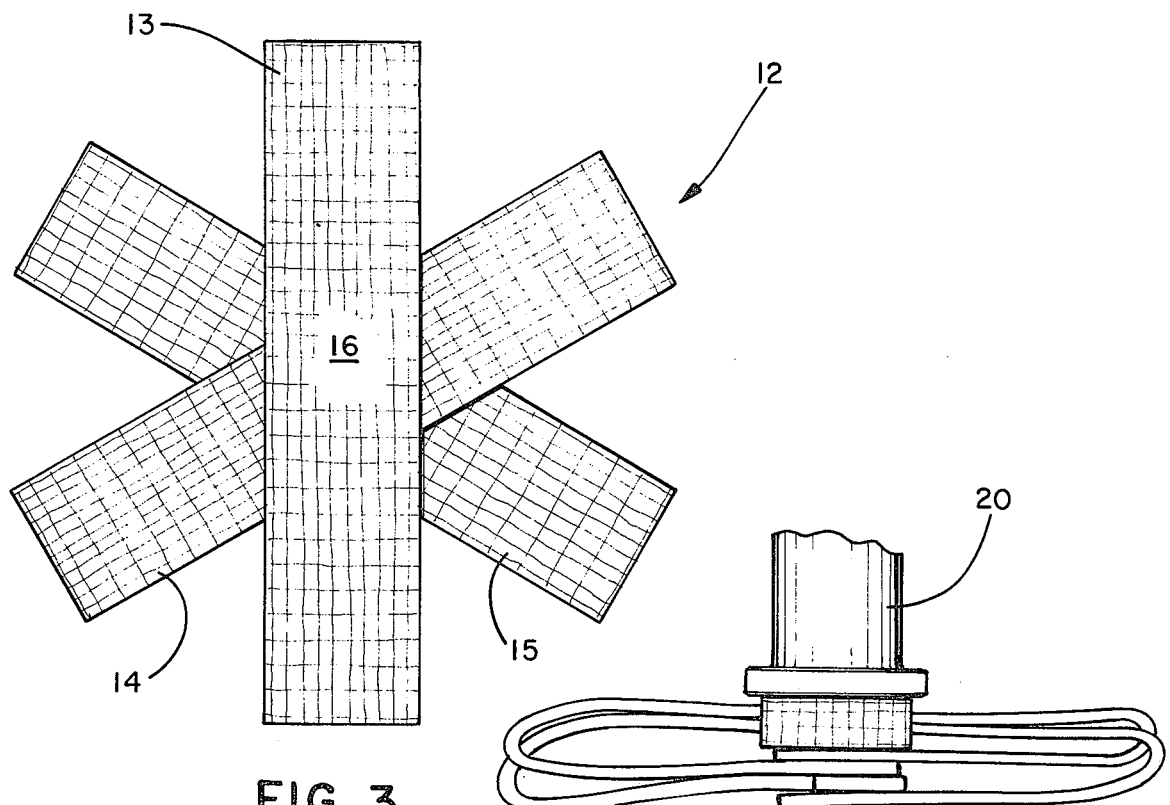
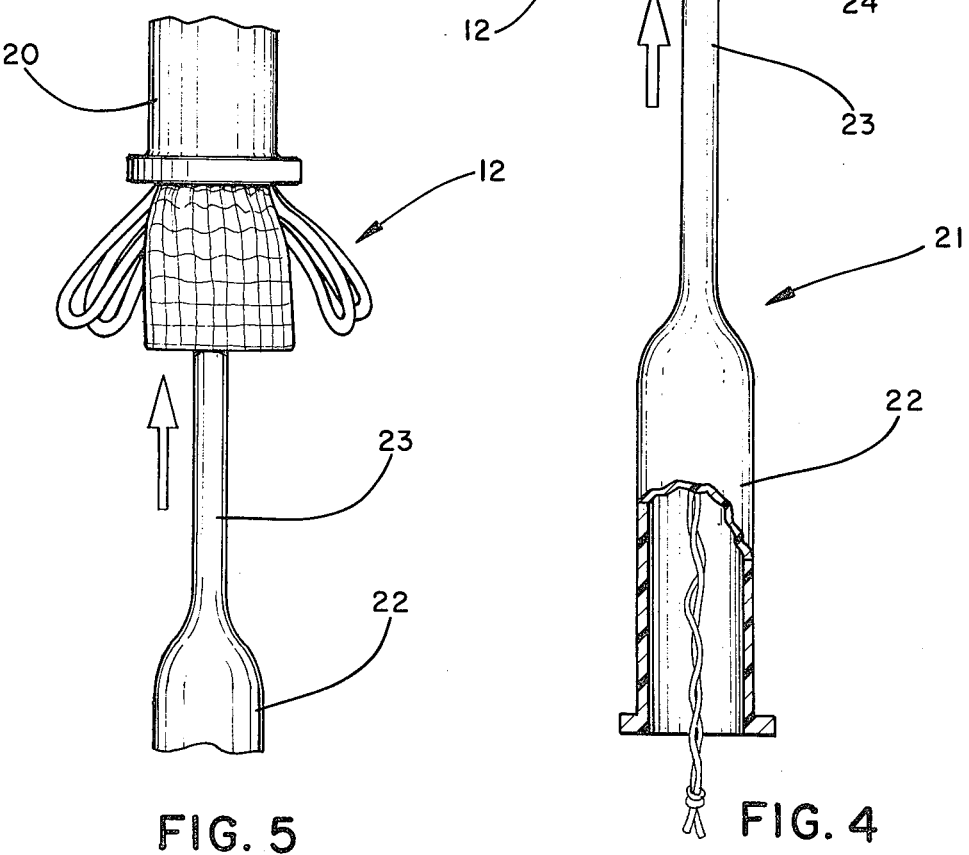

LOW DENSITY TAMPON OF INTERMESHED DEFORMABLE STRIP MATERIAL AND INSERTER THEREFOR

BACKGROUND OF THE INVENTION

It is known that absorbent tampons made of soft, low density, relatively uncompressed, resiliently deformable materials, and especially of materials such as hydrophilic or mensesphilic polyurethane foams, not only provide high absorbent capacity for menstrual exudate but also protect against early leakage. This is attributed to the fact that uncompressed low density materials are in their most effective absorbent state from the start and do not have to be acted upon, or depend on expansion activating agents, to expand to useful size. In addition, the uncompressed material has surface areas which more readily accept exudate than do the hardened surface areas of conventional compressed tampons. Further the inherent springy resiliency such foams possess enable these foams to conform more readily to the multiple irregular folds, ridges and valleys of the vaginal walls when the walls are in their normal collapsed state thus reducing the possibilities for bypass leakage through unobstructed channels. While high pressures exerted by the walls on any particular portion of the foam will compress the foam considerably in that particular area, immediately adjacent wall areas which exert lesser pressure compress the very resilient foam correspondingly less, and the tendency of the foam to expand to its normal uncompressed condition, will help it fill any voids which exist.

This invention is directed to a tampon made from such resiliently deformable materials. The described structure is one which has been found particularly effective in filling the vaginal cavity after insertion. An inserter designed to hold the tampon in resiliently deformed condition for delivery into the vagina is also described.

SUMMARY OF THE INVENTION

This invention is directed to a resiliently deformable low density tampon comprised of a multiplicity of intermeshed loops of thin flat strips made up of thin sheets of resiliently deformable absorbent material. By resiliently deformable is meant a material which in its dry condition readily deforms under relatively light loads but which returns to its uncompressed condition when the loads are removed.

The intermeshed loops of the tampon of this invention are disposed in a manner to form an openwork spheroid in which portions of the loops cross over each other at the top and bottom of the vertical axis of the spheroid. A withdrawal string is attached to the loops in the area where the loops cross at the bottom of the vertical axis, securing the strips together in that bottom crossover area.

In the absence of any loading, or compressing forces which might deform the tampon in any way, the tampon will tend to return to its spheroidal shape.

For insertion into the vaginal cavity the tampon is resiliently deformed to a size suitable for insertion. This is done by collapsing the spheroid along its vertical axis to bring the top and bottom crossover areas into juxtaposition thereby forming a multiplicity of flat loops radiating out from the crossover areas in a substantially planar arrangement. The outer extremities formed by the loops in this planar configuration are then bent downwardly from the central crossover areas to form the tampon into an inverted cup shape. The inside of this cup-shaped tampon has an internal vertex against which is disposed the leading end of an elongated pusher member employed to provide firm structural internal support to the otherwise easily deformable tampon and also to insert the tampon.

When providing its support and insertion function, the pusher member is part of an inserter device particularly useful in placing the tampon within the vaginal cavity. The inserter device comprises a pair of telescoping elements in which the outer element is in the form of an elongate tube and the inner element has an elongate lower portion slidably disposed within the tube and is provided with a frontal extension of smaller diameter than the lower portion. This frontal extension forms the pusher member. In assembling the tampon and inserter, the leading end of the pusher member is disposed against the internal vertex of the resiliently deformable, and now cup-shaped tampon, and pushed into the outer tube element which is of a smaller restricting diameter than the uncompressed cup-shaped tampon. Sliding the tampon into the restricted diameter tube resiliently compresses the cup-shaped tampon radially within the tube.

When putting the tampon to use, the outer tube is inserted in the vagina to a suitable depth, and the tampon then pushed or ejected from the tube by moving the pusher member forward and exerting force against the internal vertex of the tampon. When the trailing edges of the tampon are drawn through the outer tube and escape the restrictive confinement of the tube, the tampon will tend to expand to its uncompressed condition, and in so doing will substantially conform to the vaginal cavity. While the natural tendency of the tampon is to attempt to regain its spheroidal shape, it cannot do so because when confined in the tube the lower half of the sphere was inverted to form the internal vertex of the cup-shaped form.

Since the interior of the vagina exerts pressure somewhat similar to those exerted by the tube the tampon remains in this cup-shaped form with the extremities pressing against the vaginal walls. However when the tampon is ready for removal the withdrawal string first exerts force on the crossed strips at the bottom crossover area. This permits the lower half of the tampon to re-invert toward its original spheroidal shape which contributes to easy withdrawal.

Other embodiments and advantages of the invention will become apparent by reference to the accompanying drawings and detailed description.

BRIEF DESCRIPTION OF THE DRAWINGS

In the drawings:

FIG. 3 is a top plan view of the tampon of FIGS. 1 and 2 showing how it appears with the spheroid flattened preparatory to introducing the tampon into the outer delivery tube of an inserter device.

FIG. 4 is a side view partially cut away of the flattened tampon of FIG. 3 in association with the inserter members showing the first step in combining the tampon with an inserter device.

FIG. 5 is a partial side view showing the tampon partially introduced into the outer delivery tube of the inserter device.

DETAILED DESCRIPTION OF THE DRAWINGS AND PREFERRED EMBODIMENTS

Figure 1:
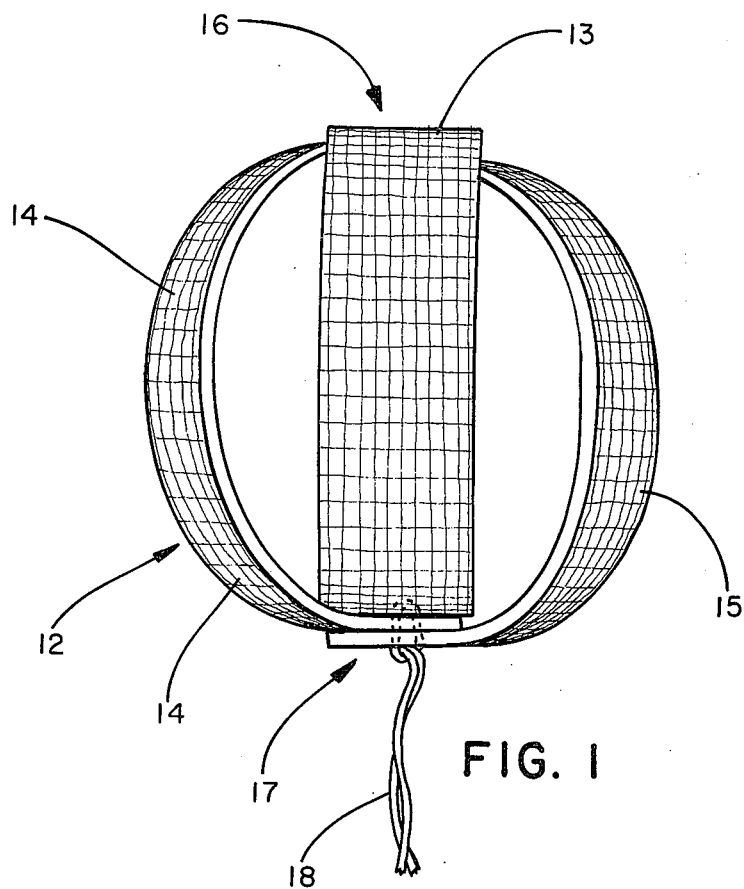
FIG. 1 is a side view of one embodiment of the spheroidal loop tampon of this invention.
Figure 2:
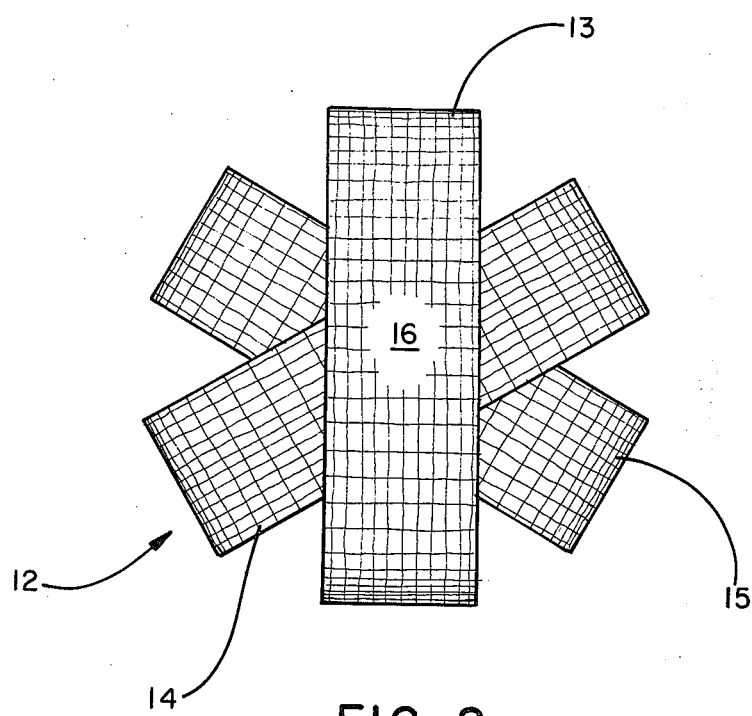
FIG. 2 is a top plan view of the tampon of FIG. 1.

Reference is first made to FIGS. 1 and 2 of the drawings in which there is shown a side and top plan view respectively of a preferred embodiment of the spheroidal loop tampon of this invention.

As shown therein, tampon 12 is made up of intermeshing loops, 13, 14 and 15 of thin, resiliently deformable absorbent strip material to form a tampon having an openwork spheroidal shape. The loops cross over each other at the top 16 and bottom 17 on the vertical axis of the spheroid. A withdrawal string 18 is attached to and secures together the loops where they cross each other at the bottom 17 of the vertical axis. The substantially spheroidal shape typifies the configuration which the loop tampon of this invention assumes when it is in its unrestricted, undeformed condition, which may be oblong or oblate. While this figure shows the tampon in its undeformed configuration, it should be noted here that the tampon assumes this particular shape only at the time of manufacture and when withdrawn from the vagina after use.

When being prepared for use and for disposition within a suitable delivery or insertion device, the spheroidal shape is first flattened as shown in the top plan view of FIG. 3. An outer tubular element 20 which will receive the tampon in resiliently deformed condition is then positioned on top of the flattened spheroidal tampon concentric with the vertical axis thereof as shown in FIG. 4. An elongate pusher element 21 comprising a widened bottom portion 22 dimensioned for slidable engagement within outer tube 20, and a lesser diameter frontal extension 23 has the leading end 24 positioned against the bottom crossover area of the flattened tampon concentric with its vertical axis. The elongate pusher element is shown as being hollow to accommodate the withdrawal string therein, but other string accommodating means can easily be provided.

With the elements of the assembly positioned as indicated in FIG. 4, the elongate pusher element 21 is advanced in the direction indicated by the arrow, thereby stuffing tampon 12 into the restricted confines of outer tube 20 and maintaining the tampon 12 in the outer tube in internally supported but resiliently deformed condition.

Figure 6:
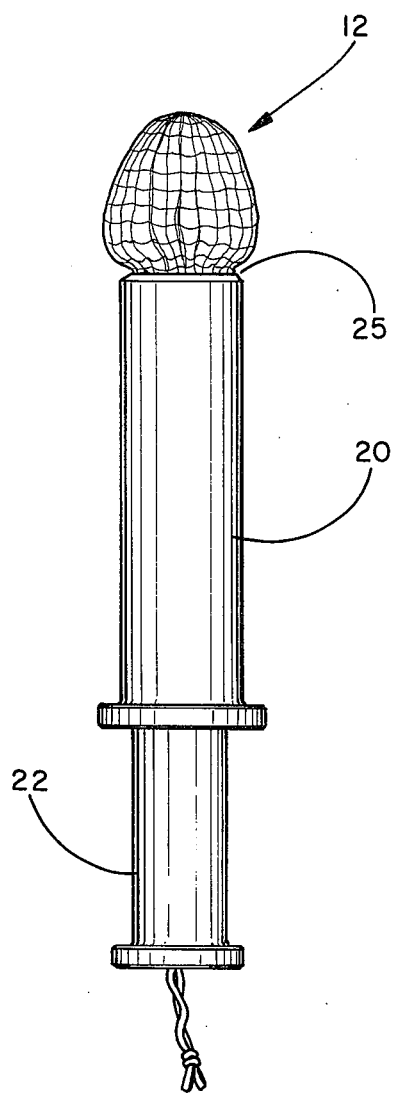
FIG. 6 is a side view of the tampon fully disposed within a suitable inserter device.
Figure 7:
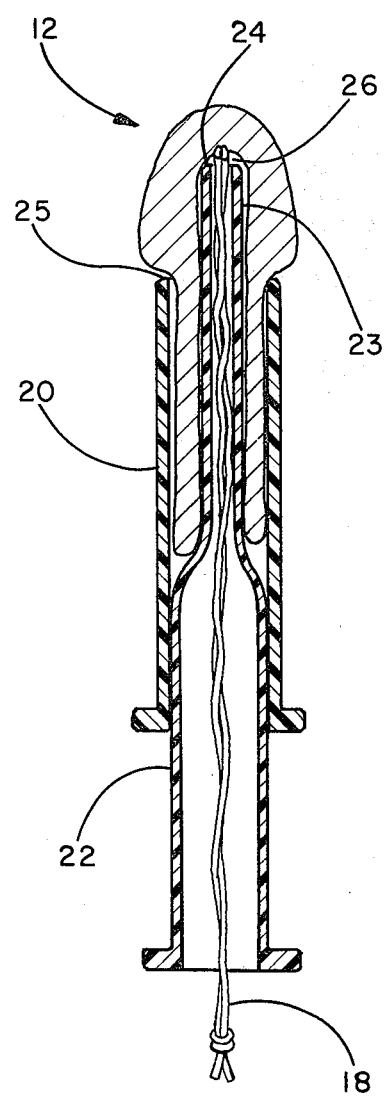
FIG. 7 is a longitudinal section of FIG. 6.

In FIG. 6, the tampon and inserter assembly is shown as it appears when fully assembled and when outer tube 20 is open-ended at its forward end 25. Since tampon 12 is of resiliently deformable material, that portion of the tampon which extends beyond forward end 25 of tube 20 and is free of restriction trys to expand to its uncompressed condition. That part of the tampon is, of course, unsuccessful in obtaining complete decompression but its partially successful effort results in a bulbous configuration somewhat as shown.

It is understood that outer tube 20 may be made long enough to contain the entire length of the tampon and have none of the tampon protrude therefrom, or it may be made shorter than shown whereby a major portion of the tampon protrudes from the end. In any event outer tube 20 must be of such length that a rear portion of the tampon remains resiliently deformed while in the tube in order that the tampon will be of a size which may be comfortably inserted into the vaginal opening.

When tampon 12 is resiliently deformed within outer tube element 20 it is in the shape of an inverted cup. The internal vertex 26 of the inverted cup rests on the leading end 24 of pusher element 21. When tampon 12 is ejected from tube element 20 by pushing against its internal vertex 26, the tampon substantially retains this inverted cup shape even though its inherent resiliency exerts force which try, unsuccessfully, of course, to reform the tampon to its uncompressed shape. The reason the tampon maintains its cup shape while in position in the vagina is that, as is well known, the internal confines of the vagina in its collapsed condition are not much larger than the dimensions of conventionally sized insertion tubes. As a result the vagina itself continually resists expansion of the tampon. While any resilient material inserted into the vaginal cavity will try to expand, and if resiliently deformable will tend to fill the available space, the material will still generally maintain the shape or form in which it was inserted because of the resistance to expansion provided by the vaginal walls. Accordingly, the tampon described herein will substantially maintain its inverted cup shape after ejection into the vagina. However, the outer edges of the cup will be continuously trying to expand and in so doing substantially fill the vagina wherever natural voids occur. The tampon also tends to expand further when fluid is absorbed thus still further improving its cavity-blocking function.

Because in the preferred embodiment, the withdrawal string is attached only to the crossed over strips disposed at the bottom of the intermeshing loops, when withdrawal force is exerted on the strips in this area by pulling on the string, such force will often cause the inner half of the inverted cup to evert and return to its original configuration. In cases where this happens, the tampon will then resume an elongated spheroidal shape at it is extracted. This eversion of the interior of the cup-shape reduces the overall bulk and makes removal of the tampon relatively easy.

In constructing the tampon, all of the loops may be made from a single continuous strip of material in which case the looped tampon in its spheroidal form will have only two free ends to be secured when the withdrawal string is attached at the bottom crossover area. Alternatively, each loop may be made of a single strip with overlapped or butted ends joined together to form each loop.

Figure 8:
FIG. 8 is a section taken through one form of strip material suitable for use in making the loop tampon of this invention.

The strip material may comprise only one ply of resiliently deformable material, or it may comprise a multiplicity of thin plys. When a polyurethane foam strip is used as the base material the tampon may be formed solely of the foam material as indicated in FIG. 8, or the foam may be strengthened by some form of internal reinforcement such as scrim or the like. In either case, the foam itself will be the absorbent body which contacts the interior of the vagina.

Figure 9:
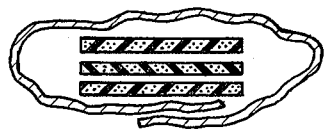
FIG. 9 is a section taken through another form of strip material suitable for use in this invention.

In a preferred form, polyurethane foam is used in the form of a strip which may comprise a single thickness or multiple thicknesses as shown in FIG. 9 and is covered with a loosely encircling fluidpervious fabric wrapper. The wrapper may be woven or non-woven and may also be hydrophilic or hydrophobic, many types of which are well known in the art. The foam strip is loosely wrapped in order not to interfere with, or restrict its potential expansion capabilities.

When the foam strips are thus wrapped, the potential frictional contact between the resiliently deformed tampon and the outer tube element is considerably reduced as compared to foam along, thus making ejection of the tampon easier. The wrapper also reinforces the foam, and is particularly useful when weak foams are employed.

The insertion device may be made of any suitable material with some flexibility but sufficient rigidity to perform the necessary functions of containment and ejection. A preferred material is a thermoplastic synthetic material such as polypropylene or polyethylene. Other plastics such as nylon, polyesters and polyvinyls may also be used but generally are not as economically acceptable because of higher fabricating and material costs. Cardboard or paperboard materials may also be employed.

While in the preferred embodiments and in the drawings the outer tube element 20 of the inserter device is shown as an open-ended tube, it is understood that the outer tube element may have a substantially closed end of the type now being marketed in which the forward end of the tube comprises a plurality of juxtaposed petal-like flexible segments which open outward when the tampon is ejected therefrom. This closed end style of inserter will, of course, not provide the swabbing action which the open-ended tube structure permits.

While the preferred embodiment shown in the drawing has three intermeshing loops, tampons made from two or more loops may also be used and generally should be evenly spaced so that the spheroidal configuration does not have uneven gaps.

Having now generally described various structural forms the tampon of this invention may take, the following description covers a particularly preferred example:

Three individual multi-ply strips of hydrophilic polyurethane foam were used. Each strip was 1 inch wide by 10 inches long and was comprised of three thinner strips each 0.060 inch thick. Each multiply strip was loosely wrapped in a non-woven 5 × 12 scrim material having a cotton fiber overlay on the outer surface. The strips were formed into loops and the loops intermeshed into a spheroidal shape as shown in FIGS. 1 and 2, with the ends which are overlapped at the bottom to complete the loop joined together at the bottom of the tampon by means of a withdrawal string. The tampon was then flattened and as shown in the drawings pushed, into an outer tube element of polypropylene having an inner diameter 11/16 inch and an outer diameter of ¾ inch. The absorbent elements of the assembled tampon, including foam strips and wrapper weighed about 3.7 grams. These tampons were then used by members of a clinical panel for catamenial use and compared with conventional tampons.

The conventional tampons tested were super size KOTEX COMFORTUBE Tampons. Such tampons are comprised of a batt of fibers consisting of 20% 3 denier rayon staple, 20% 5.5 denier rayon staple and 60% cotton linters. This batt, which is about 3½ inches long, 1½ inches wide and 3 inches thick weighs about 3.25 grams and is enclosed in a non-woven 5 × 12 scrim material having a cotton fiber overlay. The wrap material weighed about 0.5 grams per tampon. The tampon was compressed and a density of 0.85 and a size about 1½ inches long and ⅝ inch in diameter, and weighed about 3.75 grams.

| | Average Protection Time to Failure HOURS | Average Amount Absorbed to Failure GRAMS | Accumulated Leaks to 7 Hours in % HOURS | | | | | | | |
|---|---|---|---|---|---|---|---|---|---|---|
| | | | 0 | 1 | 2 | 3 | 4 | 5 | 6 | 7 |
| Conventional Tampons | 3.3 | 8.7 | 6.6 | 14.8 | 29.6 | 42.7 | 46.0 | 55.8 | 64.0 | 70.6 |
| Tampon Example Described Herein | 4.3 | 12.4 | 1.4 | 9.6 | 17.8 | 24.6 | 34.2 | 38.3 | 45.1 | 64.3 |

As indicated above, the tampon of this invention, as compared to a conventional super size tampon was worn an average of 1 hour longer before failure, and the average amount absorbed before failure was 3.7 grams more. In addition, the average amount of exudate absorbed was 3.4 grams of exudate per gram of material for the tampon of this invention as compared to 2.3 grams of exudate per gram of material for the super size conventional tampon.

It will be noted from the preceding data that the improved low density tampons of this invention were found more effective in reducing early leakers then were the conventional highly compressed tampons with which they were compared. In addition they were found equal to or better than most tampons with respect to total capacity and overall efficiency with respect to amount absorbed per unit weight.

It was also found that the low density tampons tested retained their inverted cup shape while being worn and in some instances when withdrawn were everted by the withdrawal string to provide easy removal as indicated.

What is claimed is:

1. A resiliently deformable catamenial tampon comprising a multiplicity of intermeshed loops of thin flat strips of low density absorbent material which is resiliently deformable in dry or wet condition, said intermeshed loops being disposed to form an openwork spheroid in which said loops cross over each other at the top and bottom of the vertical axis of said spheroid and have a withdrawal string attached at the loop crossover areas to secure together the loop areas at the bottom of said axis.

2. The catamenial tampon of claim 1 in which each loop is an independent strip of said material.

3. The catamenial tampon of claim 1 in which all of said loops are formed from a single continuous strip of said material.

4. The catamenial tampon of claim 1 in which said resilient deformable absorbent material is hydrophilic polyurethane foam.

5. The catamenial tampon of claim 4 in which said strips of polyurethane foam are enclosed in a loose wrap of fluid pervious non-woven material.

6. The catamenial tampon of claim 5 in which said non-woven material is hydrophilic.

7. The catamenial tampon of claim 5 in which said non-woven material is hydrophobic.

8. A catamenial tampon comprising a multiplicity of thin narrow strips of resiliently deformable absorbent material, said strips being crossed at their common center in a substantially equally spaced radial configuration, each of the radially arranged strips being further formed into a loop with the respective ends of each strip overlapping and being joined to each other; the joined overlaps of the strips crossing the overlaps of the other associated strips in an equally spaced radial configuration disposed below and coincident with the first mentioned crossing; and a withdrawal string attached at the overlaps to secure the overlapped portions of the strips together at the second mentioned crossing.

9. The catamenial tampon of claim 8 in which said resiliently deformable absorbent material is hydrophilic polyurethane foam.

10. The catamenial tampon of claim 8 in which said strips of polyurethane foam are enclosed in a loose wrap comprising a fluid-pervious non-woven web.

11. The catamenial tampon of claim 10 in which said non-woven web is hydrophilic.

12. The catamenial tampon of claim 10 in which said non-woven web is hydrophobic.

13. A self-expanding catamenial tampon and an inserter therefor, said tampon comprising a multiplicity of intermeshed loops of thin flat strips of absorbent material which material is resiliently deformable in dry or wet condition, said intermeshed loops being initially disposed to form an openwork spheroid in which said loops cross over each other at the top and bottom of the vertical axis of said spheroid, and said tampon has a withdrawal string securing together the loop areas where they cross over each other at the bottom of said axis, said sphere being collapsed along its vertical axis to juxtapose the top and bottom crossover areas to form a multiplicity of spaced flat loops radiating from the crossover areas, the extremities of said flat loops being depressed to form the intermeshed loops into an inverted cup-shaped tampon, the internal vertex of which is adapted to receive an elongate pusher element, an elongate pusher element having its leading end disposed against said vertex, said cup-shaped tampon being resiliently and radially deformed around said pusher element to a diameter suitable for insertion in the vagina, and an outer tubular insertion element slidably associated with said resiliently deformed tampon and said pusher element to maintain said tampon in resiliently deformed condition until said tampon is ejected therefrom.

14. The tampon and inserter of claim 13 in which said pusher element and outer tubular extension are hollow to receive said withdrawal string.

15. The tampon and inserter of claim 13 in which said pusher element and said inserter element are made of a flexible plastic.

16. The tampon and inserter of claim 15 in which said elements are made of polypropylene.

17. A self-expanding catamenial tampon and inserter therefor, said tampon comprising a multiplicity of thin narrow strips of resiliently deformable absorbent material, said strips being crossed at their common center in a substantially equally spaced radial configuration, each of the radially arranged strips being further formed into a loop with the respective ends of each strip overlapping and being joined to each other; the joined overlaps of the strips crossing the overlaps of the other associated strips in an equally spaced radial configuration disposed below and coincident with the first mentioned crossing; a withdrawal string attached at the overlaps to secure the overlapped portions of the strips together at the second mentioned crossing; when combined with an inserter, the crossed multiple loop structure is flattened to juxtapose the two crossing areas; the outside ends of the thus flattened loops are depressed downward to form a cup-like configuration with the withdrawal string depending from the inside vertex of the cup; the cup-like configuration is radially and resiliently compressed to a diameter suitable for insertion into the vaginal cavity and is held against self-induced reexpansion from such resiliently compressed condition by a tubular restraining member; a pusher element having a rod-like extension on its forward end is disposed in sliding association with said tubular restraining element; the leading end of said rod-like extension is disposed in contact with the inside vertex of the cup-like configured tampon structure; the thus-disposed rod-like extension of said pusher element serves as a tampon-supporting element within the restraining member as well as the means for ejecting the tampon from the restraining member.

18. The tampon and inserter of claim 17 in which said pusher element and outer tubular extension are hollow to receive said withdrawal string.

19. The tampon and inserter of claim 17 in which said pusher element and said inserter element are made of a flexible plastic.

20. The tampon and inserter of claim 19 in which said elements are made of polypropylene.

* * * * *

UNITED STATES PATENT AND TRADEMARK OFFICE
CERTIFICATE OF CORRECTION

PATENT NO. : 3,981,305
DATED : September 21, 1976
INVENTOR(S) : David F. Ring

It is certified that error appears in the above-identified patent and that said Letters Patent are hereby corrected as shown below:

Column 4, line 42, "at" should read -- as --.
Column 5, line 6, "along" should read -- alone --.
Column 6, The table should be preceded by the following:
-- The following results were recorded: --.

Signed and Sealed this

Fourteenth Day of December 1976

[SEAL]

Attest:

RUTH C. MASON
Attesting Officer

C. MARSHALL DANN
Commissioner of Patents and Trademarks